United States Patent
Chung et al.

(10) Patent No.: US 12,290,588 B2
(45) Date of Patent: May 6, 2025

(54) PEPTIDE HAVING ACTIVITY OF IMPROVING SKIN CONDITION AND USE THEREOF

(71) Applicant: CAREGEN CO., LTD., Anyang-Si (KR)

(72) Inventors: Yongji Chung, Gunpo-si (KR); Eun Mi Kim, Yongin-si (KR); Eung Ji Lee, Anyang-si (KR); Hana Kang, Anyang-si (KR)

(73) Assignee: CAREGEN CO., LTD., Anyang-si (KR)

( * ) Notice: Subject to any disclaimer, the term of this patent is extended or adjusted under 35 U.S.C. 154(b) by 541 days.

(21) Appl. No.: 17/629,272

(22) PCT Filed: Oct. 10, 2019

(86) PCT No.: PCT/KR2019/013263
§ 371 (c)(1),
(2) Date: Jan. 21, 2022

(87) PCT Pub. No.: WO2021/033829
PCT Pub. Date: Feb. 25, 2021

(65) Prior Publication Data
US 2022/0241174 A1    Aug. 4, 2022

(30) Foreign Application Priority Data

Aug. 20, 2019  (KR) .................. 10-2019-0101877

(51) Int. Cl.
| | |
|---|---|
| *A61K 8/64* | (2006.01) |
| *A61K 38/00* | (2006.01) |
| *A61P 29/00* | (2006.01) |
| *A61Q 19/00* | (2006.01) |
| *A61Q 19/08* | (2006.01) |
| *C07K 7/06* | (2006.01) |

(52) U.S. Cl.
CPC ................ *A61K 8/64* (2013.01); *A61P 29/00* (2018.01); *A61Q 19/004* (2013.01); *A61Q 19/08* (2013.01); *C07K 7/06* (2013.01); *A61K 38/00* (2013.01)

(58) Field of Classification Search
CPC . A61K 8/64; A61K 38/00; A61P 29/00; A61P 17/00; A61P 17/06; A61P 17/08; A61P 17/10; A61Q 19/004; A61Q 19/08; A61Q 19/00; C07K 7/06; Y02P 20/55
See application file for complete search history.

(56) References Cited

U.S. PATENT DOCUMENTS

| | | |
|---|---|---|
| 5,516,891 A | 5/1996 | Siwruk et al. |
| 10,047,125 B2 | 8/2018 | Chung et al. |
| 11,103,436 B2 | 8/2021 | Chung et al. |
| 2017/0146548 A1 | 5/2017 | Hickok et al. |
| 2020/0002377 A1 | 1/2020 | Van Den Nest et al. |

FOREIGN PATENT DOCUMENTS

| | | |
|---|---|---|
| EP | 1335743 B1 | 12/2009 |
| KR | 10-1043081 B1 | 6/2011 |
| KR | 10-1104223 B1 | 1/2012 |
| KR | 10-2013-0083103 A | 7/2013 |
| KR | 10-2015-0130616 A | 11/2015 |
| KR | 10-2016-0069054 A | 6/2016 |
| KR | 10-1900747 B1 | 9/2018 |
| KR | 10-1943081 B1 | 1/2019 |
| KR | 10-2019-0085136 A | 7/2019 |
| WO | WO-2010/105636 A1 | 9/2010 |
| WO | WO-2014/144129 A2 | 9/2014 |

OTHER PUBLICATIONS

Extended European Search Report dated Mar. 7, 2023, for European Patent Application No. 19941864.1, Chung et al., "Peptide Having Activity of Improving Skin Condition and Use Thereof," filed Oct. 10, 2019 (5 pages).

Notice of Allowance dated May 3, 2021, for Korean Application No. 10-2019-0101877, Jeong et al., "The peptide having the skin condition improvement activity and use thereof" (partial English translation) (7 pages).

Notice of Reason for Refusal dated Jan. 6, 2021, for Korean Application No. 10-2019-0101877, Jeong et al., "The peptide having the skin condition improvement activity and use thereof" (English translation) (10 pages).

*Primary Examiner* — Marcela M Cordero Garcia
(74) *Attorney, Agent, or Firm* — Clark & Elbing LLP

(57) ABSTRACT

Provided are a peptide having an activity of improving skin condition and use thereof. In particularly, provided are a peptide consisting of an amino acid sequence of SEQ ID NO: 1, a cosmetic composition including the peptide for improving skin condition, and a pharmaceutical composition including the peptide for preventing or treating an inflammatory skin disease.

7 Claims, 8 Drawing Sheets
Specification includes a Sequence Listing.

PEPTIDE HAVING ACTIVITY OF IMPROVING SKIN CONDITION AND USE THEREOF

SEQUENCE LISTING

The instant application contains a Sequence Listing which has been submitted electronically in ASCII format and is hereby incorporated by reference in its entirety. Said ASCII copy, created on Jan. 20, 2022, is named 51401-032001_Sequence_Listing_1_20_22_ST25 and is 5,220 bytes in size.

TECHNICAL FIELD

The present disclosure relates to a peptide having an activity of improving skin condition and use thereof.

BACKGROUND ART

Human skin is constantly undergoing changes, and the most representative changes are decreased skin function and loss of visual beauty due to aging. Aging forms wrinkles in the skin, and representative wrinkle-forming factors include exposure to ultraviolet light and reduced collagen biosynthesis. Skin aging is largely divided into intrinsic aging according to genetic factors and extrinsic aging according to external environmental factors such as sunlight. In particular, in the case of extrinsic aging, the aging is known to be prevented, treated, or delayed through removal of active oxygen, proliferation of fibroblasts, and promotion of collagen biosynthesis.

Collagen, which is a main component of the extracellular matrix, is a main matrix protein produced in fibroblasts of the skin. Collagen forms most of organic materials of skin, tendons, bones, and teeth, and bones and skin (dermis) particularly include high collagen content. However, collagen is reduced by age and photoaging by ultraviolet irradiation, and such reduction is known to be closely related to the wrinkle formation in the skin. In addition, collagen plays an important role in wound healing. In detail, collagen promotes the collagen synthesis in the damaged epithelium to quickly restore wound without leaving a scar. Furthermore, it has been reported that a melanin pigment concentration per unit the skin density is lowered when the collagen density in basement membranes is increased upon the promoted collagen biosynthesis. In this regard, effects of collagen on brightening the skin tone can be expected.

Under such technical background, various studies are in progress to improve skin condition through mechanisms including promoting collagen biosynthesis, proliferating fibroblasts, and enhancing cellular activity (Korean Patent No. 10-1043081), but the study process is incomplete yet.

DESCRIPTION OF EMBODIMENTS

Technical Problem

An aspect of the present disclosure provides a peptide consisting of an amino acid sequence of SEQ ID NO: 1.

Another aspect of the present disclosure provides a cosmetic composition for improving skin condition, the composition including the peptide as an active ingredient.

Another aspect of the present disclosure provides a pharmaceutical composition for preventing or treating an inflammatory skin disease, the composition including the peptide as an active ingredient.

Other purposes and advantages of the present disclosure will become more obvious with the following detailed description, claims, and drawing. Contents not described herein will be sufficiently recognized and inferred by those skilled in the technical field of the present application or in a similar technical field therewith, and thus descriptions of such contents will be omitted.

Solution to Problem

Description and embodiments disclosed herein may also be applied to other descriptions and embodiments, respectively. That is, all combinations of various elements disclosed herein belong to the scope of the present disclosure. In addition, the scope of the present application is not construed to be limited by the detailed description provided below.

An aspect of the present disclosure provides a peptide consisting of an amino acid sequence of SEQ ID NO: 1.

The term "peptide" as used herein refers to a linear molecule in which amino acid residues bind to each other via a peptide linkage. The peptide may be prepared by chemical synthesis methods known in the art, particularly, solid-phase synthesis techniques (Merrifield, J. Amer. Chem. Soc. 85:2149-54 (1963); Stewart, et al., Solid Phase Peptide Synthesis, 2nd. ed., Pierce Chem. Co.: Rockford, 111 (1984)) or liquid-phase synthesis techniques (U.S. Pat. No. 5,516,891). The inventors of the present disclosure endeavored to develop a peptide having biologically effective activity, and consequently established a peptide consisting of an amino acid sequence of SEQ ID NO: 1. Here, such biologically effective activity may include one or more characteristics selected from: (a) inhibition of apoptosis of fibroblasts and keratinocytes; (b) promotion of collagen synthesis; (c) inhibition of expression of matrix metalloproteases; (d) restoration of activity of fibroblasts and keratinocytes; and (e) inhibition of expression of inflammatory cytokines. In this regard, the peptide may be used for the purpose of improving skin condition or preventing or treating an inflammatory skin disease.

To obtain chemical stability, enhanced pharmacological properties (e.g., half-life, absorbency, titer, efficacy, etc.), modified specificity (e.g., broad spectrum of biological activity), and reduced antigenicity, an N-terminus or a C-terminus of the peptide may be bound to a protecting group. In an embodiment, the N-terminus of the peptide may be bound to any one protecting group selected from the group consisting of an acetyl group, a fluoreonylmethoxycarbonyl group, a formyl group, a palmitoyl group, a myristyl group, a stearyl group, a butoxycarbonyl group, an allyloxycarbonyl group, and polyethylene glycol (PEG); and/or the C-terminus of the peptide may be bound to any one protecting group selected from the group consisting of an amino group ($-NH_2$), a tertiary alkyl group, and an azide group ($-NHNH_2$). In addition, the peptide may optionally further include an amino acid sequence that is prepared for a particular purpose to increase stability of a target sequence, a tag, a labeled residue, a half-life, or a peptide.

The term "stability" as used herein refers to storage stability (e.g., room temperature storage stability) as well as in vivo stability that protects the peptide from the attack of in vivo proteolytic enzymes.

Another aspect of the present disclosure provides: a cosmetic composition including, as an active ingredient, the peptide including the amino acid sequence of SEQ ID NO: 1; a pharmaceutical composition including, as an active ingredient, the peptide including the amino acid sequence of SEQ ID NO: 1; and use of the peptide including the amino acid sequence of SEQ ID NO: 1 to prepare a cosmetic or pharmaceutical composition or to be used as a cosmetic or pharmaceutical composition.

Another aspect of the present disclosure provides a cosmetic composition for improving skin condition, the composition including the peptide consisting of the amino acid sequence of SEQ ID NO: 1 as an active ingredient.

Overlapping terms or elements with those already mentioned in the description of the peptide are the same as described above.

The term "improvement" as used herein refers to parameters associated with alleviation or treatment of the condition, and for example, refers to any action that at least reduce severity of a symptom.

The term "improvement of skin condition" as used herein comprehensively refers to a process of treating, alleviating, or relaxing skin damage caused by intrinsic or extrinsic factors of the skin, or effects of the process. For example, the improvement of skin condition may be construed as representing wrinkle relief, skin elasticity improvement, wound regeneration, skin aging inhibition, or alleviation of inflammatory skin disease, but is not limited thereto.

The terms "wrinkle relief", "skin elasticity improvement", and "wound regeneration" as used herein refer to any action including promoting collagen synthesis or the like that can increase the total amount of collagen in the skin. In addition, the term "skin aging inhibition" as used herein refers to inhibition of decrease in skin functions, such as wrinkles, sagging skin, reduced elasticity, and the like. Here, the skin aging may be photoaging, for example, skin aging caused by ultraviolet light. In addition, the term "alleviation of an inflammatory skin disease" as used herein refers to any action including inhibition of expression of inflammatory cytokines or the like that can alleviate or improve an inflammatory response of the skin caused physiologically or pathologically.

A functional peptide in the art had disadvantages in that it was not effectively introduced into target tissues or cells due to the size of the peptide itself despite its effective biological activity, or it disappeared from the body in a short period of time due to a short half-life. Meanwhile, the cosmetic composition according to an embodiment includes, as an active ingredient, a peptide consisting of 10 or less amino acids, and thus the active ingredient may have high skin penetration rates. For example, when topically applied onto the skin, the skin condition may be effectively improved.

In an embodiment, the peptide may increase the cellular activity of fibroblasts and promote the collagen synthesis. In addition, the peptide show effects of inhibiting apoptosis of fibroblasts and keratinocytes, inhibiting expression or activity of matrix metalloproteases increased by ultraviolet light, and restoring activity of fibroblasts and keratinocytes lowered by ultraviolet light. In this regard, the peptide may be utilized as an active ingredient in the cosmetic composition for improving the skin condition.

The cosmetic composition may include: a cosmetically effective amount of the peptide; and/or a cosmetically acceptable carrier, but embodiments of the present disclosure are not limited thereto.

The term "cosmetically effective amount" as used herein refers to an amount that is sufficient to attain efficacy of the cosmetic composition in the improvement of the skin condition.

A weight ratio of the peptide and the cosmetically acceptable carrier may be, for example, in a range of about 500:1 to about 1:500, and in an embodiment, in a range of about 450:1 to about 1:450, about 400:1 to about 1:400, about 350:1 to about 1:350, about 300:1 to about 1:300, about 250:1 to about 1:250, about 200:1 to about 1:200, about 150:1 to about 1:150, about 100:1 to about 1:100, about 80:1 to about 1:80, about 60:1 to about 1:60, about 40:1 to about 1:40, about 20:1 to about 1:20, about 10:1 to about 1:10, about 8:1 to about 1:8, about 6:1 to about 1:6, about 4:1 to about 1:4, or about 2:1 to about 1:2, but embodiments of the present disclosure are not limited thereto.

The cosmetic composition may be prepared in any formulation type conventionally prepared in the art. For example, the cosmetic composition may be formulated into a solution, a suspension, an emulsion, a paste, a gel, a cream, a lotion, a powder, a soap, a surfactant-containing cleansing, an oil, a powder foundation, an emulsion foundation, a wax foundation, a spray, and the like, but embodiments of the present disclosure are not limited thereto. For example, the cosmetic composition may be prepared in the formulation of emollient lotion, nourishing lotion, nourishing cream, massage cream, essence, eye cream, cleansing cream, cleansing foam, cleansing water, mask pack, spray, or powder.

When the formulation of the cosmetic composition is a paste, a cream, or a gel, an animal oil, a plant oil, wax, paraffin, starch, tragacanth, a cellulose derivative, polyethylene glycol, silicone, bentonite, silica, talc, or zinc oxide may be used as a carrier component.

When the formulation of the cosmetic composition is a powder or a spray, lactose, talc, silica, aluminum hydroxide, calcium silicate, or a polyamide powder may be used as the carrier component. For example, in cases where the formulation is a spray, the spray may further include a propellant, such as chlorofluorohydrocarbon, propane/butane, or dimethyl ether.

In cases where the formulation is a solution or an emulsion, a solvent, a solubilizer, or an emulsifier may be used as the carrier component, and examples of the carrier component are water, ethanol, isopropanol, ethyl carbonate, ethyl acetate, benzyl alcohol, benzyl benzoate, propylene glycol, 1,3-butylglycol oil, glycerol fatty ester, polyethylene glycol, or fatty acid ester of sorbitan.

In cases where the formulation is a suspension, a liquid diluent (such as water, ethanol, or propylene glycol), a suspending agent (such as ethoxylated isostearyl alcohol, polyoxyethylene sorbitol ester, and polyoxyethylene sorbitan ester), microcrystalline cellulose, aluminum metahydroxide, bentonite, agar, or tragacanth may be used as the carrier component.

In cases where the formulation is a surfactant-containing cleansing, aliphatic alcohol sulfate, aliphatic alcohol ether sulfate, sulfosuccinate monoester, isethionate, an imidazolinium derivative, methyl taurate, sarcosinate, fatty acid amide ether sulfate, alkyl amido betaine, aliphatic alcohol, fatty acid glyceride, fatty acid diethanolamide, plant oil, a lanoline derivative, or ethoxylated glycerol fatty acid ester may be used as the carrier component.

The components included in the cosmetic composition may include, in addition to the peptide as an active ingredient and the carrier component, components that are commonly used in the cosmetic composition. For example, the components may include common auxiliary agents, such as an antioxidant, a stabilizer, a solubilizer, a vitamin, a pigment, and a flavor.

Another aspect of the present disclosure provides a method of improving skin condition, the method including applying the cosmetic composition onto the skin of a subject, wherein the cosmetic composition includes, as an active ingredient, the peptide consisting of the amino acid sequence of SEQ ID NO: 1.

Overlapping terms or elements with those already mentioned in the description of the cosmetic composition are the same as described above.

The terms "applying", "administering", and "coating" are used interchangeably, and may be construed as causing at least partial localization by the composition according to an embodiment onto a desired site, or arranging the composition according to an embodiment into a subject by the administration route.

Another aspect of the present disclosure provides a pharmaceutical composition for preventing or treating an inflammatory skin disease, the composition including the peptide as an active ingredient.

Overlapping terms or elements with those already mentioned in the description of the peptide are the same as described above.

The term "prevention" as used herein refers to any action that can inhibit or delay the onset of a disease by administration of the composition.

The term "treatment" as used herein refers to any form of treatment that provides, to a subject afflicted with or at risk of developing a disease, effects including improving conditions (e.g., one or more symptoms) of the subject, delaying progression of a disease, delaying onset of symptoms, or slowing progression of symptoms. That is, the terms "treatment" and "prevention" are not intended to mean cure or complete elimination of symptoms.

The term "subject" as used herein refers to a target in need of disease treatment, and more particularly, refers to a mammal including a human or a non-human primate, such as a mouse, a dog, a cat, a horse, and a cow.

The "inflammatory skin disease" which is a target disease to be prevented or treated by using the pharmaceutical composition may be a generic term for skin diseases having inflammation as a main lesion. Examples of the inflammatory skin disease are acne, atopic dermatitis, psoriasis, seborrheic dermatitis, contact dermatitis, lupus erythematosus, or papular urticarcia, but are not limited thereto.

In an embodiment, the peptide show effects of inhibiting expression or activity of matrix metalloproteases increased by ultraviolet light, restoring activity of fibroblasts and keratinocytes lowered by ultraviolet light, and inhibiting expression of an inflammatory factor increased by ultraviolet light. In this regard, the peptide may be utilized as an active ingredient in the pharmaceutical composition for preventing or treating an inflammatory skin disease.

The pharmaceutical composition may include: a pharmaceutically effective amount of the peptide; and/or a pharmaceutically acceptable carrier, but embodiments of the present disclosure are not limited thereto.

The term "pharmaceutically effective amount" as used herein refers to an amount that is sufficient to attain efficacy of the pharmaceutical cosmetic composition in the prevention or treatment of an inflammatory skin disease.

A weight ratio of the peptide and the pharmaceutically acceptable carrier may be, for example, in a range of about 500:1 to about 1:500, and in an embodiment, in a range of about 450:1 to about 1:450, about 400:1 to about 1:400, about 350:1 to about 1:350, about 300:1 to about 1:300, about 250:1 to about 1:250, about 200:1 to about 1:200, about 150:1 to about 1:150, about 100:1 to about 1:100, about 80:1 to about 1:80, about 60:1 to about 1:60, about 40:1 to about 1:40, about 20:1 to about 1:20, about 10:1 to about 1:10, about 8:1 to about 1:8, about 6:1 to about 1:6, about 4:1 to about 1:4, or about 2:1 to about 1:2, but embodiments of the present disclosure are not limited thereto.

The pharmaceutically acceptable carrier may be conventionally used at the time of formulation, and examples thereof are lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and the like, but are not limited thereto. Suitable pharmaceutically acceptable carriers and agents are described in detail in Remington's Pharmaceutical Sciences (19th ed., 1995).

The pharmaceutical composition may further include, in addition to the ingredients above, a lubricant, a wetting agent, a sweetening agent, a flavoring agent, an emulsifier, a suspending agent, a preservative, and the like, but is not limited thereto.

The pharmaceutical composition may be administered orally or parenterally, and preferably parenterally. Examples of the parenteral administration are intramuscular, intravenous, subcutaneous, intraperitoneal, local, and transdermal injections, but are not limited thereto.

A dose of the pharmaceutical composition may be in a range of about 0.0001 microgram (ug) per day to about 1,000 ug per day, about 0.001 ug per day to about 1,000 ug per day, about 0.01 ug per day to about 1,000 ug per day, about 0.1 ug per day to about 1,000 ug per day, or about 1.0 ug per day to about 1,000 ug per day, but is not limited thereto. The dose may be prescribed in various ways depending on factors, such as the method of formulation, the manner of administration, the age, body weight, gender, and morbidity of a patient, the, the time of administration, the route of administration, the excretion rate, and the response sensitivity.

The pharmaceutical composition may be formulated into a unit dosage form or prepared in a multi-dose container by formulating a pharmaceutically acceptable carrier and/or excipient according to the method easily carried out by a person having ordinary skill in the art to which the present invention pertains.

Here, the dosage form may be a solution in an oily or aqueous medium, a suspension, an emulsion, an extract, a powder, a granule, a tablet, or a capsule, and may further include a dispersant and/or a stabilizer.

Another aspect of the present disclosure provides a method of preventing or treating an inflammatory skin disease, the method including administering, to a subject, the pharmaceutical composition, wherein the pharmaceutical composition includes, as an active ingredient, the peptide consisting of the amino acid sequence of SEQ ID NO: 1.

Overlapping terms or elements with those already mentioned in the description of the pharmaceutical composition are the same as described above.

Another aspect of the present disclosure provides a food composition for improving skin condition, the composition including, as an active ingredient, the peptide consisting of the amino acid sequence of SEQ ID NO: 1.

Overlapping terms or elements with those already mentioned in the description of the peptide are the same as described above.

An amount of the peptide which is included as an active ingredient in the food composition may be appropriately selected without limitation depending on the type of food, desired use, and the like. For example, the peptide may be added in an amount of 0.01 wt % to about 15 wt % based on the total food weight. Also, for example, the health beverage composition may be added in a proportion of about 0.02 g to about 10 g, preferably about 0.3 g to about 1 g, based on 100 ml of the peptide.

Advantageous Effects of Disclosure bβ

A peptide according to an aspect may be applied for improving skin conditions including wrinkle relief, skin elasticity improvement, wound regeneration, skin aging suppression, and the like by increasing cellular activity of fibroblasts and promoting collage synthesis.

A peptide according to an aspect may be applied for alleviating or improving an inflammatory response of the skin by restoring inhibited activity of fibroblasts and keratinocytes and inhibiting expression of inflammatory cytokines.

Therefore, a peptide according to an aspect may be utilized as an active ingredient in a cosmetic composition for improving skin condition or in a pharmaceutical composition for preventing or treating an inflammatory skin disease.

MODE OF DISCLOSURE

Hereinafter, the present disclosure will be described in detail with reference to Examples below. However, these Examples are provided for illustrative purposes only, and the scope of the present disclosure is not limited thereto.

Example 1. Synthesis of Peptide

A peptide having an amino acid sequence of SEQ ID NO: 1 of Table 1 was synthesized by using an automatic peptide synthesizer Milligen 9050 (Millipore, USA). Then, C18 reverse-phase high-performance liquid chromatography (HPLC) (Waters Associates, USA) was performed thereon to purely separate the synthesized peptide. Here, ACQUITY UPLC BEH300 C18 column (2.1 mm×100 mm, 1.7 μm, Waters Co, USA) was used.

TABLE 1

| SEQ ID NO. | Sequence (5'->3') |
|---|---|
| 1 | ECEELEEK |

Example 2. Confirmation of Effect of Increasing Expression of Procollagen 1α

NIH3T3 mouse fibroblasts were seeded in a 6-well plate at a density of $5 \times 10^3$ cells/well, and cultured for 16 hours. Afterwards, the culture medium was replaced with a serum-free medium, the peptide consisting of the amino acid sequence of SEQ ID NO: 1 was added thereto at a concentration of 10 μM, 50 μM, or 100 μM, and the cells were cultured for 24 hours. Then, the amount of procollagen 1α in the medium was measured by using a Procollagen 1α ELISA kit (Us biological lifescience, USA). Meanwhile, a non-treated group (Con) was used as a control group, and a group to which 100 nM of bFGF was added and a group to which 5 ng/ml of TGF-β1 was added were used as positive control groups.

Figure 1:
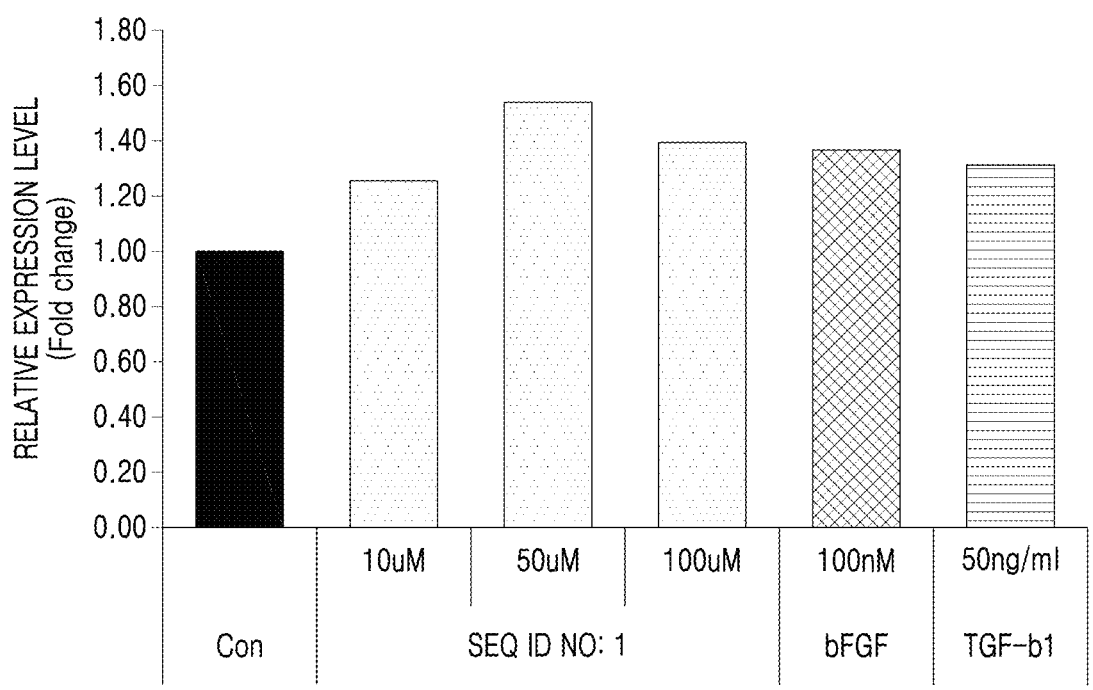
FIG. 1 shows a result confirming the increased expression of procollagen 1α after adding a peptide consisting of an amino acid sequence of SEQ ID NO: 1 to fibroblasts.

As a result, as shown in FIG. 1, it was confirmed that the expression of procollagen 1α, which is a factor related to collagen synthesis in fibroblasts, was increased by the addition of the peptide consisting of the amino acid sequence of SEQ ID NO: 1.

Example 3. Confirmation of Effect of Enhancing Activity of Fibroblasts

In this example, an effect the peptide according to an embodiment on the cellular activity of fibroblasts was to be confirmed by measuring the expression levels of PPAR-γ, PPAR-δ, and PGC-1α, which are mitochondrial biogenesis-related genes. In detail, NIH3T3 mouse fibroblasts were seeded in a 6-well plate at a density of $3 \times 10^5$ cells/well, and cultured for 16 hours. Afterwards, the culture medium was replaced with a serum-free medium, the peptide consisting of the amino acid sequence of SEQ ID NO: 1 was added thereto at a concentration of 10 μM, 50 μM, or 100 μM, and the cells were cultured for 24 hours. Then, mRNA was extracted from the cultured cells, and reverse-transcribed into cDNA by using a cDNA synthesis kit and PCR pre-mix (Intron, Korea). Afterwards, a polymerase chain reaction (PCR) was performed by using the cDNA and primers of PPAR-γ, PPAR-δ, and PGC-1α. Meanwhile, a control group and positive groups were used in the same manner as in Example 2, and the nucleotide sequences of the primers used herein are shown in Table 2.

TABLE 2

| Primer | | Sequence (5'->3') | SEQ ID NO. |
|---|---|---|---|
| PPAR-γ | Foward | ACGATCTGCCTGAGGTCTGT | 2 |
| | Reverse | CATCGAGGACATCCAAGACA | 3 |
| PPAR-δ | Foward | CTGAAGGGAAGGGGGTAGAG | 4 |
| | Reverse | CAGTCTGGATGCTGCTACA | 5 |
| PGC-1α | Foward | ACTGAGCTACCCTTGGGATG | 6 |
| | Reverse | TAAGGATTTCGGTGGTGACA | 7 |

TABLE 2-continued

| Primer | | Sequence (5'->3') | SEQ ID NO. |
|---|---|---|---|
| GAPDH | Foward | GGTGTGAACGGATTTGGCCGTATTG | 8 |
| | Reverse | CCGTTGAATTTGCCGTGAGTGGAGT | 9 |

Figure 2:
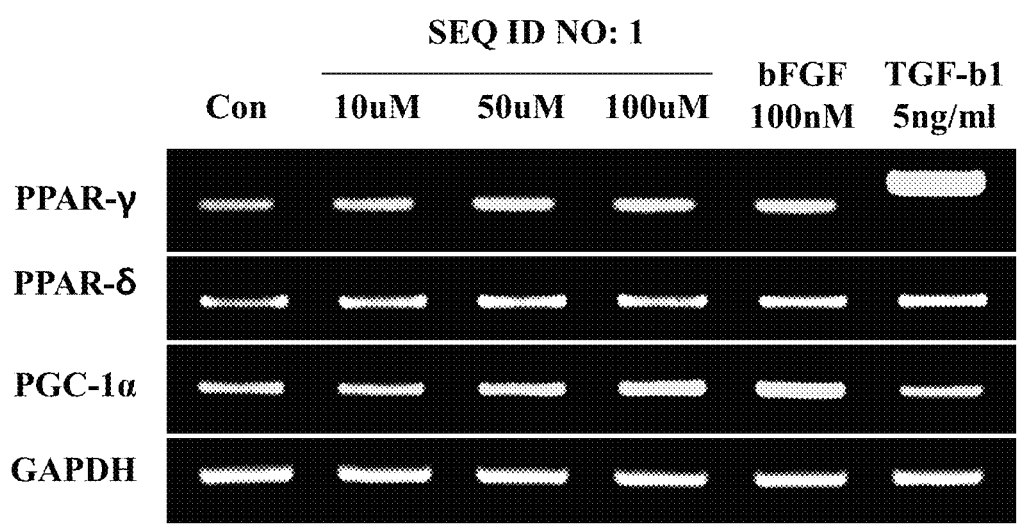
FIG. 2 shows a result confirming the increased expression of PPAR-γ, PPAR-δ, and PGC-1α after adding the peptide to fibroblasts.

As a result, as shown in FIG. 2, it was confirmed that the expression of PPAR-γ, PPAR-δ, and PGC-1α, which are factors related to the cellular activity of fibroblasts, was increased by the addition of the peptide consisting of the amino acid sequence of SEQ ID NO: 1. Referring to these results, it was confirmed that the peptide according to an embodiment contributed to improving skin conditions including wrinkle relief, skin elasticity improvement, wound regeneration, and the like by increasing the cellular activity of fibroblasts and promoting collagen synthesis.

Figure 3:
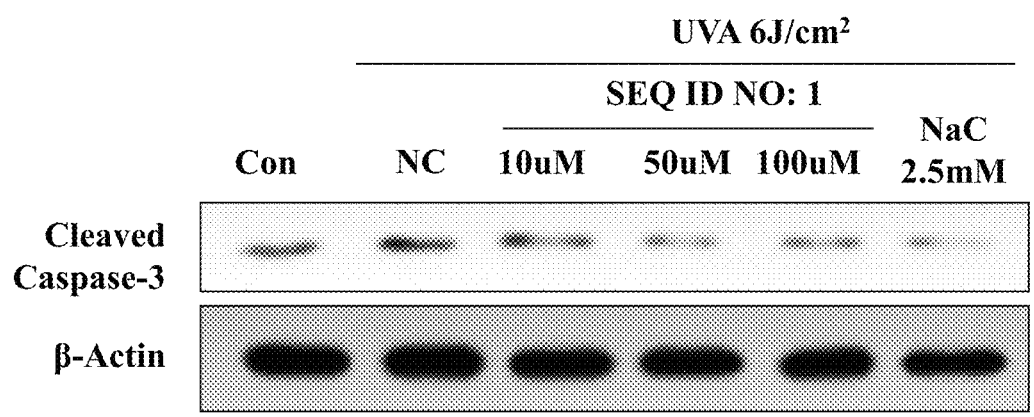
FIG. 3 shows a result confirming the decreased expression of cleaved caspase-3, which is increased by ultraviolet irradiation, after adding the peptide to fibroblasts.
Figure 4:
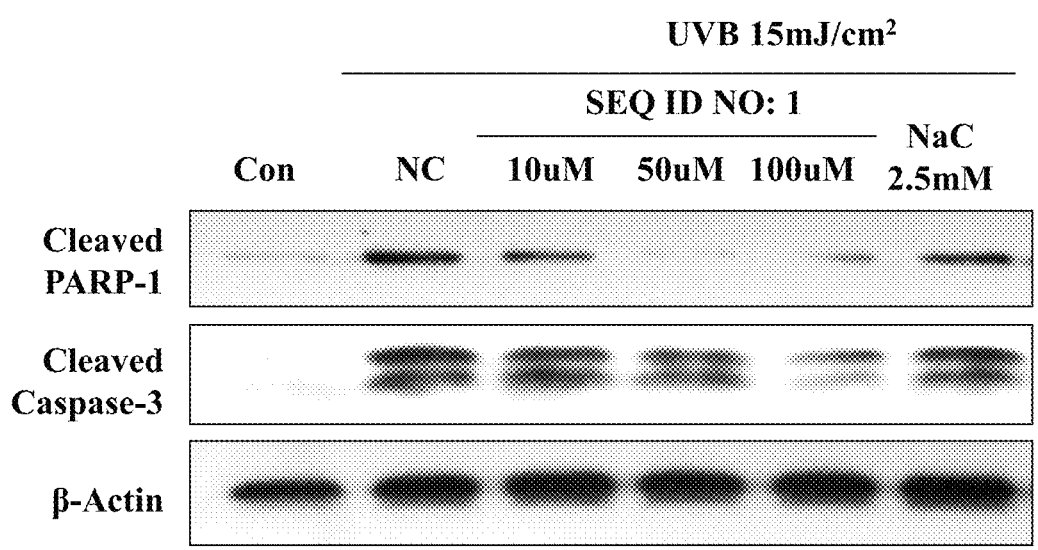
FIG. 4 shows a result confirming the decreased expression of cleaved PARP-1 and cleaved caspase-3, which are increased by ultraviolet irradiation, after adding the peptide to keratinocytes.

Example 4. Confirmation of Inhibitory Effect on Apoptosis of Fibroblasts and Keratinocytes NIH3T3 mouse fibroblasts or HaCaT human keratinocytes were respectively seeded in a 6-sell plate at a density of 3×10$^5$ cells/well, and cultured for 16 hours. Afterwards, the culture medium was replaced with a serum-free medium, the peptide consisting of the amino acid sequence of SEQ ID NO: 1 was added thereto at a concentration of 10 μM, 50 μM, or 100 μM, and the cells were cultured for 1 hour. Each well containing the cultured cells was washed with phosphate buffered saline (PBS), and the NIH3T3 cells or HaCaT cells were respectively irradiated with ultraviolet light of 6 J/cm$^2$ or 15 J/cm$^2$, so as to induce an increase in the expression of apoptosis proteins. Afterwards, the culture medium was replaced with a serum-free medium, the peptide consisting of the amino acid sequence of SEQ ID NO: 1 was added thereto at a concentration of 10 μM, 50 μM, or 100 μM, and the cells were cultured for 24 hours. Cell lysates were obtained by adding a lysis buffer to the cultured cells, and then, western blotting was performed thereon by using cleaved PARP-1 and cleaved caspase-3 antibodies (Santacruz biotechnology, USA). Meanwhile, a non-treated group (Con) was used as a control group. For use as a negative control group and a positive control group, a non-treated group after ultraviolet irradiation (NC), and a group to which 2.5 mM of NaC was added after ultraviolet irradiation were used, respectively As a result, as shown in FIGS. 3 and 4, it was confirmed that the expression of cleaved caspase-3 which was increased by ultraviolet irradiation in the fibroblasts was reduced by the addition of the peptide having the amino acid sequence of SEQ ID NO: 1. As such, it was confirmed that the expression of cleaved PARP-1 and cleaved caspase-3 which were increased by ultraviolet irradiation in the keratinocytes was significantly reduced. Referring these results, it was confirmed that the peptide according to an embodiment was able to inhibit apoptosis of the skin cells.

Example 5. Confirmation of Inhibitory Effect on Matrix Metalloprotease Increased by Ultraviolet Light NIH3T3 mouse fibroblasts were seeded in a 6-well plate at a density of 3×10$^5$ cells/well, and cultured for 16 hours. Afterwards, the culture medium was replaced with a serum-free medium, the peptide consisting of the amino acid sequence of SEQ ID NO: 1 was added thereto at a concentration of 10 μM, 50 μM, or 100 μM, and the cells were cultured for 1 hour. Each well containing the cultured cells was washed with PBS, and the NIH3T3 cells were irradiated with ultraviolet light of 6 J/cm$^2$, so as to induce an increase in the expression of MMP-1 and MMP-2. Afterwards, the culture medium was replaced with a serum-free medium, the peptide consisting of the amino acid sequence of SEQ ID NO: 1 was added thereto at a concentration of 10 μM, 50 μM, or 100 μM, and the cells were cultured for 24 hours. Afterwards, cell lysates were obtained by adding a lysis buffer to the cultured cells, and then, western blotting was performed thereon by using MMP-1 antibodies (cell signaling, USA) to measure the expression of MMP-1.

Meanwhile, the cell lysates were subjected to gelatin zymography to measure the activity of MMP-2. In detail, after protein electrophoresis (SDS-PAGE) was performed by using 2 mg/ml of gelatin as a substrate. Following the electrophoresis, the gel was treated with 2.5% Triton X-100 for 30 minutes, and then incubated in a buffer containing 50 mM Tris-HCl, 0.2 M NaCl, 5 mM CaCl$_2$, and 1% Triton X-100 at 37° C. for 24 hours. Afterwards, the gel was stained with Coo-massie Brilliant Blue R250 (Sigma), and destained with a buffer containing 5% methanol, 7.5% acetic acid, and distilled water. Then, the bands formed by gelatin hydrolysis were observed with naked eyes. Meanwhile, a control group, a negative control group, and a positive control group were used in the same manner as in Example 4.

Figure 5:
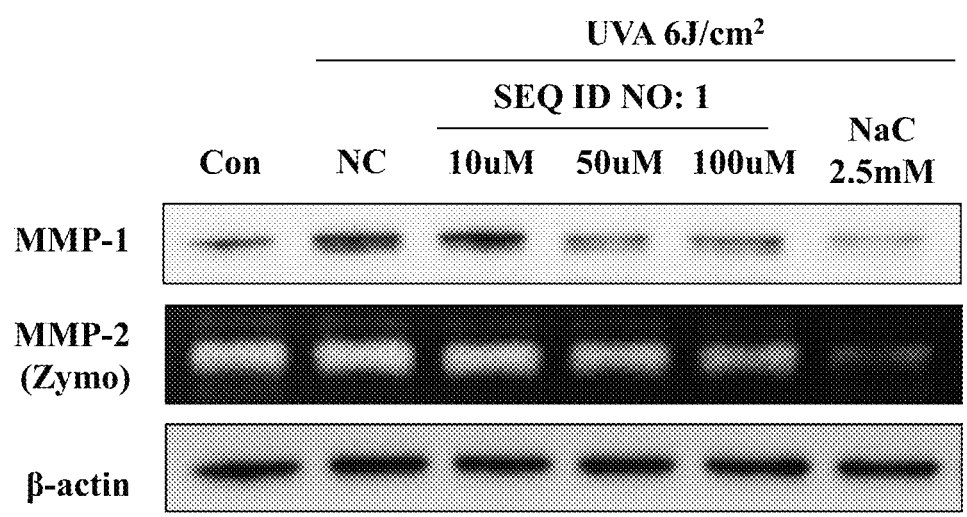
FIG. 5 shows a result confirming decreased expression of MMP-1 and the decreased activity of MMP-2, which are increased by ultraviolet irradiation, after adding the peptide to fibroblasts.

As a result, as shown in FIG. 5, it was confirmed that the expression of MMP-1 and the activity of MMP-2 which were increased by ultraviolet irradiation in the fibroblasts were reduced by the addition of the peptide having the amino acid sequence of SEQ ID NO: 1.

Example 6. Confirmation of Restoration Effect on Cellular Activity of Fibroblasts and Keratinocytes Inhibited by Ultraviolet Light In this example, changes in the cellular activity of fibroblasts were evaluated through the expression of Col1a1, Fibronectin, and Elastin, which are known as components of the dermis. Also, changes in the cellular activity of keratinocytes were evaluated through the expression of SIRT1, which is an anti-aging gene, and AQP3, which is a component of the skin barrier. Based on the evaluation results, the effect of the peptide according to an embodiment on the restoration of the cellular activity of the fibroblasts and keratinocytes was confirmed. In detail, NIH3T3 mouse fibroblasts or HaCaT human keratinocytes were respectively seeded in a 6-sell plate at a density of 3×10$^5$ cells/well, and cultured for 16 hours. Afterwards, the culture medium was replaced with a serum-free medium, the peptide consisting of the amino acid sequence of SEQ ID NO: 1 was added thereto at a concentration of 10 μM, 50 μM, or 100 μM, and the cells were cultured for 1 hour. Each well containing the cultured cells was washed with PBS, and the NIH3T3 cells or the HaCaT cells were respectively irradiated with ultraviolet light of 6 J/cm$^2$ or 20 J/cm$^2$, so as to induce inhibition of the cellular activity. Afterwards, the culture medium was replaced with a serum-free medium, the peptide consisting of the amino acid sequence of SEQ ID NO: 1 was added thereto at a concentration of 10 μM, 50 μM, or 100 μM, and the cells were cultured for 6 hours. Then, mRNA was extracted from the cultured cells, and reverse-transcribed into cDNA by using a cDNA synthesis kit and PCR pre-mix (Intron, Korea). Afterwards, PCR was performed by using: the cDNAs derived from the fibroblasts and primers of Col1 at Fibronectin, and Elastin; and the cDNAs derived from the keratinocytes and primers of SIRT1 and AQP3. Meanwhile, a control group, a negative group, and a positive group were used in the same manner as in Example 4, and the nucleotide sequences of the primers used herein are shown in Tables 3 and 4.

TABLE 3

| Primer | | Sequence (5'->3') | SEQ ID NO. |
|---|---|---|---|
| Col1a1 | Foward | CACCCTCAAGAGCCTGAGTC | 10 |
| | Reverse | AGACGGCTGAGTAGGGAACA | 11 |
| Fibronectin | Foward | CCAGGAACCGAGTACACCAT | 12 |
| | Reverse | ATACCCAGGTTGGGTGATGA | 13 |
| Elastin | Foward | GGACCCCTGACTCGCGACCT | 14 |
| | Reverse | GGGGAGGTGGGACTGCCCAA | 15 |
| GAPDH | Foward | GGTGTGAACGGATTTGGCCGTATTG | 8 |
| | Reverse | CCGTTGAATTTGCCGTGAGTGGAGT | 9 |

TABLE 4

| Primer | | Sequence (5'->3') | SEQ ID NO. |
|---|---|---|---|
| SIRT1 | Foward | TCAGTGGCTGGAACAGTGAG | 16 |
| | Reverse | TCTGGCATGTCCCACTATCA | 17 |
| AQP3 | Foward | CCTTCTTGGGTGCTGGAATA | 18 |
| | Reverse | ACACGATAAGGGAGGCTCTG | 19 |
| GAPDH | Foward | GGTGTGAACGGATTTGGCCGTATTG | 8 |
| | Reverse | CCGTTGAATTTGCCGTGAGTGGAGT | 9 |

Figure 6:
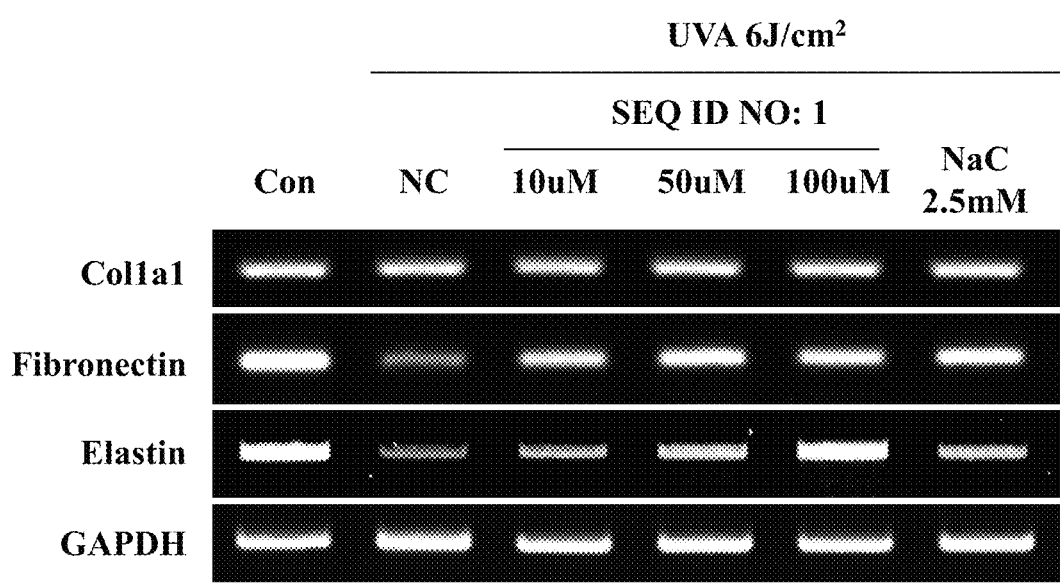
FIG. 6 shows a result confirming the increased expression of Col1 a1, Fibronectin, and Elastin, which are decreased by ultraviolet irradiation, after adding the peptide to fibroblasts.
Figure 7:
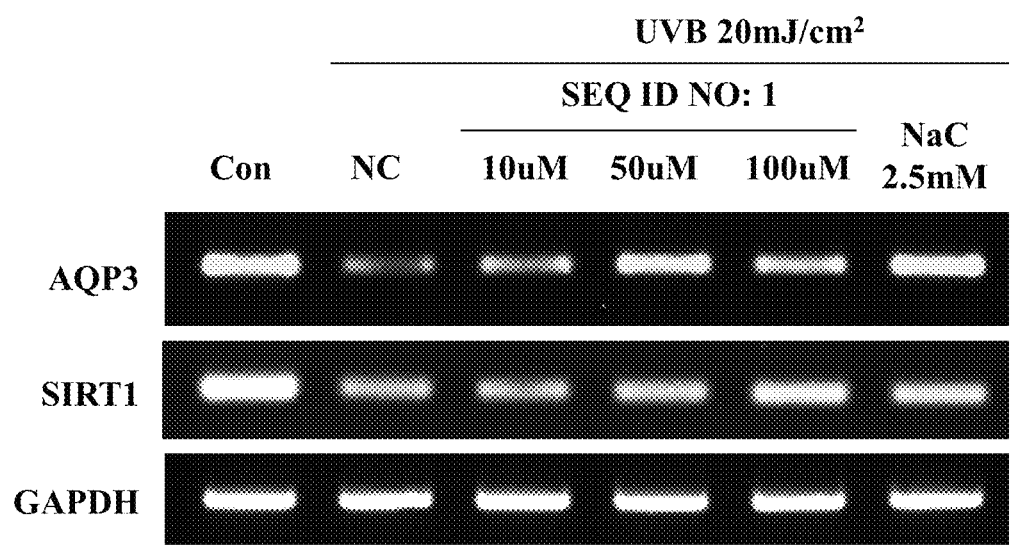
FIG. 7 shows a result confirming the increased expression of SIRT1 and AQP3, which are decreased by ultraviolet irradiation, after adding the peptide to keratinocytes.

As a result, as shown in FIGS. 6 and 7, it was confirmed that the expression of Col1 a1, Fibronectin, and Elastin which were inhibited by ultraviolet irradiation in fibroblasts was restored back to normal levels by the addition of the peptide consisting of the amino acid sequence of SEQ ID NO: 1. As such, it was also confirmed that the expression of SIRT1 and AQP3 which were reduced by ultraviolet irradiation in keratinocytes was restored. Based on these results, it was found that the peptide according to an embodiment contributed to improving the pathological environment of the skin, including decreased density of the dermal layer and decreased skin barrier, by restoring the cellular activity of the damaged skin cells.

Example 7. Confirmation of Inhibitory Effect on Expression of Inflammatory Factor Increased by Ultraviolet Rays HaCaT human keratinocytes were seeded in a 6-well plate at a density of 3×10$^5$ cells/well, and cultured for 16 hours. Afterwards, the culture medium was replaced with a serum-free medium, the peptide consisting of the amino acid sequence of SEQ ID NO: 1 was added thereto at a concentration of 10 μM, 50 μM, or 100 μM, and the cells were cultured for 1 hour. Each well containing the cultured cells was washed with PBS, and the HaCaT cells were irradiated with ultraviolet light of 15 J/cm$^2$, so as to induce an increase in the expression of inflammatory cytokine which is an inflammatory factor. Then, mRNA was extracted from the cultured cells, and reverse-transcribed into cDNA by using a cDNA synthesis kit and PCR pre-mix (Intron, Korea). Afterwards, PCR was performed by using the cDNA and primers of TNF-α, COX-2, IL-1β, and IL-6. Meanwhile, a control group and a positive group were used in the same manner as in Example 4, and the nucleotide sequences of the primers used herein are shown in Table 5.

TABLE 5

| Primer | | Sequence (5'->3') | SEQ ID NO. |
|---|---|---|---|
| TNF-α | Forward | CGTCAGCCGATTRTGCTATCT | 20 |
| | Reverse | CGGACTCCGCAAAGTCTAAG | 21 |
| | Forward | ATCATTCACCAGGCAAATTGC | 22 |
| | Reverse | GGCTTCAGCATAAAGCGTTTG | 23 |
| IL-1β | Forward | TTCGACACATGGGATAACGA | 24 |
| | Reverse | TCTTTCAACACGCAGGACAG | 25 |
| IL-6 | Forward | AAAGAGGCACTGCCAGAAAA | 26 |
| | Reverse | ATCTGAGGTGCCCATGCTAC | 27 |
| GAPDH | Forward | GGTGTGAACGGATTTGGCCGTATTG | 8 |
| | Reverse | CCGTTGAATTTGCCGTGAGTGGAGT | 9 |

Figure 8:
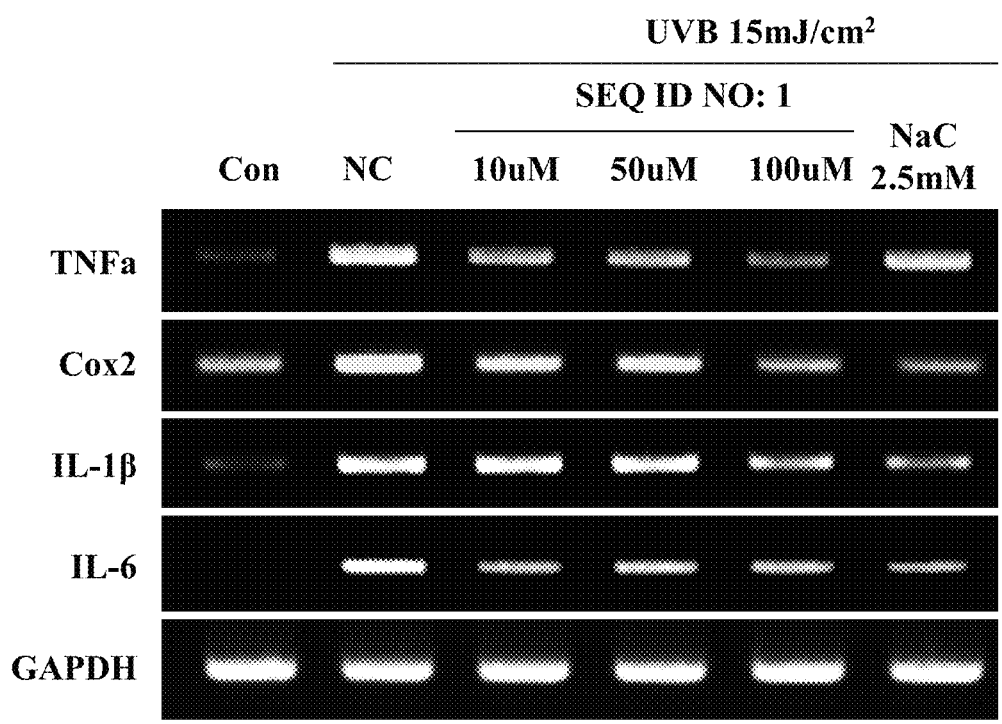
FIG. 8 shows a result confirming the decreased expression of TNF-α, COX-2, IL-1β, and IL-6, which are increased by ultraviolet irradiation, after adding the peptide to keratinocytes.

As a result, as shown in FIG. 8, it was confirmed that the expression of TNF-α, COX-2, IL-1β, and IL-6 which were increased by ultraviolet irradiation in the keratinocytes was reduced by the addition of the amino acid sequence SEQ ID NO: 1. Referring these results, it was confirmed that the peptide according to an embodiment was able to alleviate or improve the inflammatory response of the skin.

The foregoing descriptions are only for illustrating the present disclosure, and it will be apparent to a person having ordinary skill in the art to which the present invention pertains that the embodiments disclosed herein can be easily modified into other specific forms without changing the technical spirit or essential features. Therefore, it should be understood that Examples described herein are illustrative in all respects and are not limited.

The invention claimed is:

1. A method of improving skin condition, the method comprising applying, to the skin of an individual, a peptide consisting of an amino acid sequence of SEQ ID NO: 1,
wherein the improving of the skin condition is selected from wrinkle relief, skin elasticity improvement, wound regeneration, and alleviation of an inflammatory skin disease.

2. The method of claim 1, wherein the N-terminus of the peptide is bound to any one protecting group selected from the group consisting of an acetyl group, a fluoreonyl-methoxycarbonyl group, a formyl group, a palmitoyl group, a myristyl group, a stearyl group, a butoxycarbonyl group, an allyloxycarbonyl group, and polyethylene glycol (PEG).

3. The method of claim 1, wherein the C-terminus of the peptide is bound to any one protecting group selected from the group consisting of an amino group ($-NH_2$), a tertiary alkyl group, and an azide group ($-NHNH_2$).

4. The method of claim 1, wherein the peptide exhibits any one or more characteristics selected from the following:
  (a) inhibition of apoptosis of fibroblasts and keratinocytes;
  (b) promotion of collagen synthesis;
  (c) inhibition of expression of matrix metalloproteases;
  (d) restoration of activity of fibroblasts and keratinocytes; and
  (e) inhibition of expression of inflammatory cytokines.

5. A method of treating an inflammatory skin disease, the method comprising administering, to an individual, a therapeutically effective amount of a peptide consisting of an amino acid sequence of SEQ ID NO: 1,
wherein the inflammatory skin disease is selected from acne, atopic dermatitis, psoriasis, seborrheic dermatitis, contact dermatitis, lupus erythematosus, and papular urticaria.

6. The method of claim 5, wherein the N-terminus of the peptide is bound to any one protecting group selected from the group consisting of an acetyl group, a fluoreonyl-methoxycarbonyl group, a formyl group, a palmitoyl group, a myristyl group, a stearyl group, a butoxycarbonyl group, an allyloxycarbonyl group, and polyethylene glycol (PEG).

7. The method of claim 5, wherein the C-terminus of the peptide is bound to any one protecting group selected from the group consisting of an amino group ($-NH_2$), a tertiary alkyl group, and an azide group ($-NHNH_2$).

* * * * *

SEQUENCE LISTING

```
<160> NUMBER OF SEQ ID NOS: 27

<210> SEQ ID NO 1
<211> LENGTH: 8
<212> TYPE: PRT
<213> ORGANISM: Artificial Sequence
<220> FEATURE:
<223> OTHER INFORMATION: Peptide 1

<400> SEQUENCE: 1
```

Glu Cys Glu Glu Leu Glu Glu Lys
1               5

<210> SEQ ID NO 2
<211> LENGTH: 20
<212> TYPE: DNA
<213> ORGANISM: Artificial Sequence
<220> FEATURE:
<223> OTHER INFORMATION: PPAR-gamma_F

<400> SEQUENCE: 2
acgatctgcc tgaggtctgt                                           20

<210> SEQ ID NO 3
<211> LENGTH: 20
<212> TYPE: DNA
<213> ORGANISM: Artificial Sequence
<220> FEATURE:
<223> OTHER INFORMATION: PPAR-gamma_R

<400> SEQUENCE: 3
catcgaggac atccaagaca                                           20

<210> SEQ ID NO 4
<211> LENGTH: 20
<212> TYPE: DNA
<213> ORGANISM: Artificial Sequence
<220> FEATURE:
<223> OTHER INFORMATION: PPAR-delta_F

<400> SEQUENCE: 4
ctgaagggaa gggggtagag                                           20

<210> SEQ ID NO 5
<211> LENGTH: 19
<212> TYPE: DNA
<213> ORGANISM: Artificial Sequence
<220> FEATURE:
<223> OTHER INFORMATION: PPAR-delta_R

<400> SEQUENCE: 5
cagtctggat gctgctaca                                            19

<210> SEQ ID NO 6
<211> LENGTH: 20
<212> TYPE: DNA
<213> ORGANISM: Artificial Sequence
<220> FEATURE:
<223> OTHER INFORMATION: PGC-1alpha_F

<400> SEQUENCE: 6
actgagctac ccttgggatg                                           20

<210> SEQ ID NO 7
<211> LENGTH: 20
<212> TYPE: DNA
<213> ORGANISM: Artificial Sequence
<220> FEATURE:
<223> OTHER INFORMATION: PGC-1alpha_R

<400> SEQUENCE: 7
taaggatttc ggtggtgaca                                           20

<210> SEQ ID NO 8
<211> LENGTH: 25
<212> TYPE: DNA

```
<213> ORGANISM: Artificial Sequence
<220> FEATURE:
<223> OTHER INFORMATION: GAPDH_F

<400> SEQUENCE: 8
ggtgtgaacg gatttggccg tattg                                           25

<210> SEQ ID NO 9
<211> LENGTH: 25
<212> TYPE: DNA
<213> ORGANISM: Artificial Sequence
<220> FEATURE:
<223> OTHER INFORMATION: GAPDH_R

<400> SEQUENCE: 9
ccgttgaatt tgccgtgagt ggagt                                           25

<210> SEQ ID NO 10
<211> LENGTH: 20
<212> TYPE: DNA
<213> ORGANISM: Artificial Sequence
<220> FEATURE:
<223> OTHER INFORMATION: Col1a1_F

<400> SEQUENCE: 10
caccctcaag agcctgagtc                                                 20

<210> SEQ ID NO 11
<211> LENGTH: 20
<212> TYPE: DNA
<213> ORGANISM: Artificial Sequence
<220> FEATURE:
<223> OTHER INFORMATION: Col1a1_R

<400> SEQUENCE: 11
agacggctga gtagggaaca                                                 20

<210> SEQ ID NO 12
<211> LENGTH: 20
<212> TYPE: DNA
<213> ORGANISM: Artificial Sequence
<220> FEATURE:
<223> OTHER INFORMATION: Fibronectin_F

<400> SEQUENCE: 12
ccaggaaccg agtacaccat                                                 20

<210> SEQ ID NO 13
<211> LENGTH: 20
<212> TYPE: DNA
<213> ORGANISM: Artificial Sequence
<220> FEATURE:
<223> OTHER INFORMATION: Fibronectin_R

<400> SEQUENCE: 13
atacccaggt tgggtgatga                                                 20

<210> SEQ ID NO 14
<211> LENGTH: 20
<212> TYPE: DNA
<213> ORGANISM: Artificial Sequence
<220> FEATURE:
<223> OTHER INFORMATION: Elastin_F

<400> SEQUENCE: 14 ggaccccctga ctcgcgacct                                                20
```

```
<210> SEQ ID NO 15
<211> LENGTH: 20
<212> TYPE: DNA
<213> ORGANISM: Artificial Sequence
<220> FEATURE:
<223> OTHER INFORMATION: Elastin_R

<400> SEQUENCE: 15
ggggaggtgg gactgcccaa                                              20

<210> SEQ ID NO 16
<211> LENGTH: 20
<212> TYPE: DNA
<213> ORGANISM: Artificial Sequence
<220> FEATURE:
<223> OTHER INFORMATION: SIRT1_F

<400> SEQUENCE: 16
tcagtggctg gaacagtgag                                              20

<210> SEQ ID NO 17
<211> LENGTH: 20
<212> TYPE: DNA
<213> ORGANISM: Artificial Sequence
<220> FEATURE:
<223> OTHER INFORMATION: SIRT1_R

<400> SEQUENCE: 17
tctggcatgt cccactatca                                              20

<210> SEQ ID NO 18
<211> LENGTH: 20
<212> TYPE: DNA
<213> ORGANISM: Artificial Sequence
<220> FEATURE:
<223> OTHER INFORMATION: AQP3_F

<400> SEQUENCE: 18
ccttcttggg tgctggaata                                              20

<210> SEQ ID NO 19
<211> LENGTH: 20
<212> TYPE: DNA
<213> ORGANISM: Artificial Sequence
<220> FEATURE:
<223> OTHER INFORMATION: AQP3_R

<400> SEQUENCE: 19
acacgataag ggaggctctg                                              20

<210> SEQ ID NO 20
<211> LENGTH: 21
<212> TYPE: DNA
<213> ORGANISM: Artificial Sequence
<220> FEATURE:
<223> OTHER INFORMATION: TNF-alpha_F

<400> SEQUENCE: 20
cgtcagccga ttrtgctatc t                                            21

<210> SEQ ID NO 21
<211> LENGTH: 20
<212> TYPE: DNA
<213> ORGANISM: Artificial Sequence
<220> FEATURE:
```

<223> OTHER INFORMATION: TNF-alpha_R

<400> SEQUENCE: 21
cggactccgc aaagtctaag                                                    20

<210> SEQ ID NO 22
<211> LENGTH: 21
<212> TYPE: DNA
<213> ORGANISM: Artificial Sequence
<220> FEATURE:
<223> OTHER INFORMATION: COX-2_F

<400> SEQUENCE: 22
atcattcacc aggcaaattg c                                                  21

<210> SEQ ID NO 23
<211> LENGTH: 21
<212> TYPE: DNA
<213> ORGANISM: Artificial Sequence
<220> FEATURE:
<223> OTHER INFORMATION: COX-2_R

<400> SEQUENCE: 23
ggcttcagca taaagcgttt g                                                  21

<210> SEQ ID NO 24
<211> LENGTH: 20
<212> TYPE: DNA
<213> ORGANISM: Artificial Sequence
<220> FEATURE:
<223> OTHER INFORMATION: IL-1beta_F

<400> SEQUENCE: 24
ttcgacacat gggataacga                                                    20

<210> SEQ ID NO 25
<211> LENGTH: 20
<212> TYPE: DNA
<213> ORGANISM: Artificial Sequence
<220> FEATURE:
<223> OTHER INFORMATION: IL-1beta_R

<400> SEQUENCE: 25
tctttcaaca cgcaggacag                                                    20

<210> SEQ ID NO 26
<211> LENGTH: 20
<212> TYPE: DNA
<213> ORGANISM: Artificial Sequence
<220> FEATURE:
<223> OTHER INFORMATION: IL-6_F

<400> SEQUENCE: 26
aaagaggcac tgccagaaaa                                                    20

<210> SEQ ID NO 27
<211> LENGTH: 20
<212> TYPE: DNA
<213> ORGANISM: Artificial Sequence
<220> FEATURE:
<223> OTHER INFORMATION: IL-6_R

<400> SEQUENCE: 27
atctgaggtg cccatgctac                                                    20